United States Patent
Toshimitsu et al.

(10) Patent No.: US 6,434,569 B1
(45) Date of Patent: *Aug. 13, 2002

(54) INTEGRATED MEDICAL INFORMATION SYSTEM FORMED OF TEXT-BASED AND IMAGE-BASED DATABASES, AND DISPLAY THEREOF

(75) Inventors: Akihiro Toshimitsu, Otawara; Eitaro Nishihara, Toda, both of (JP)

(73) Assignee: Kabushiki Kaisha Toshiba, Kawasaki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/869,777

(22) Filed: Jun. 5, 1997

(30) Foreign Application Priority Data

Jun. 6, 1996 (JP) .............................. 8-144535

(51) Int. Cl.[7] .............................. G06F 17/30
(52) U.S. Cl. .......................... 707/104; 707/8; 707/100; 707/102
(58) Field of Search .................. 705/3; 707/2, 100, 707/101, 8, 102, 104; 345/1, 5

(56) References Cited

U.S. PATENT DOCUMENTS

| | | | |
|---|---|---|---|
| 3,970,996 A | * 7/1976 | Yasaka et al. ................. 705/3 |
| 4,737,912 A | * 4/1988 | Ichikawa .................... 600/301 |
| 5,019,976 A | * 5/1991 | Chiu et al. .................. 382/203 |
| 5,027,110 A | * 6/1991 | Chang et al. ................ 340/731 |
| 5,270,530 A | * 12/1993 | Godlewski et al. ....... 250/208.1 |
| 5,272,625 A | * 12/1993 | NIshihara et al. ............... 707/1 |
| 5,325,294 A | * 6/1994 | Keene .................... 364/413.01 |
| 5,335,173 A | * 8/1994 | Sasahara ..................... 600/407 |
| 5,551,428 A | * 9/1996 | Godlewski et al. ....... 128/653.1 |
| 5,586,262 A | * 12/1996 | Komatsu et al. ........ 395/200.02 |
| 5,605,153 A | * 2/1997 | Fujioka et al. .............. 600/425 |
| 5,615,112 A | * 3/1997 | Sheng et al. ................. 707/104 |
| 5,655,084 A | * 8/1997 | Pinsky et al. ................... 708/3 |
| 5,671,070 A | * 9/1997 | Przybylowica et al. ..... 358/487 |
| 5,671,359 A | * 9/1997 | Godlewski et al. .......... 395/203 |
| 5,713,350 A | * 2/1998 | Yokota et al. .............. 600/300 |
| 5,772,585 A | * 6/1998 | Lavin et al. ................. 600/300 |
| 5,779,634 A | * 7/1998 | Ema et al. ................... 600/407 |
| 5,793,969 A | * 8/1998 | Kamentsky et al. ... 395/200.43 |
| 5,959,678 A | * 9/1999 | Callahan et al. ............ 348/442 |
| 6,014,630 A | * 1/2000 | Jeacock et al. ................ 705/3 |

OTHER PUBLICATIONS

E. Bellon, et al. "PACS/HIS Integration in Handling and Viewing ICU Images Generated by a Phosphorplate Scanner" proceedings of SPIE Medicology Imaging 1996–PACS design and Evaluation, vol. 2711, pp. 126–136, 1996.

* cited by examiner

*Primary Examiner*—Reba I. Elmore
(74) *Attorney, Agent, or Firm*—Oblon, Spivak, McClelland, Maier & Neustadt, P.C.

(57) ABSTRACT

A medical information system has a terminal device of a hospital information system for retrieving and displaying an examination list and a reading report and an image display terminal device for displaying an image. Both terminal devices are arranged to mutually transfer the identification information of an examination to enable their displayed contents to be changed interlockingly. Therefore, medical information, such as charts, medical images, reading reports and results of examinations, required to perform a diagnosis is formed into electronic data and electronic data is displayed on a screen to provide information for a doctor.

33 Claims, 7 Drawing Sheets

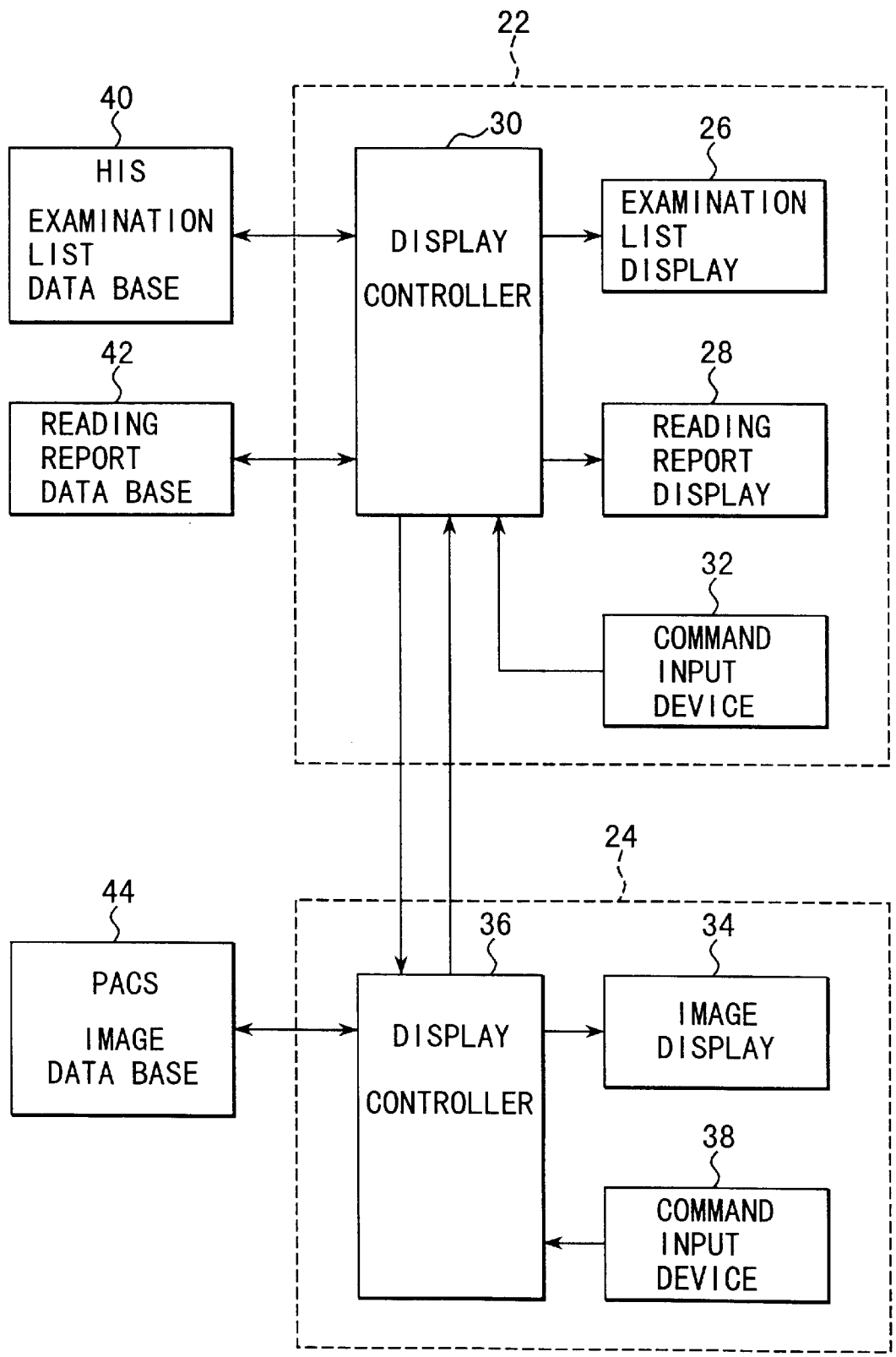
F I G. 2

| Patient ID | Name |
|---|---|
| 999801 | Hanako Nasu |
| 111111 | Taro Toshiba |
| ⋮ | ⋮ |

[Exec] 50

26

F I G. 3

| Date | Examination Name |
|---|---|
| 96/12/1 | Chest X-ray |
| 96/12/1 | Chest CT |
| 96/10/1 | Head MRI |
| 96/10/1 | Head X-ray |
| 95/12/1 | Chest X-ray |
| ------- | ------- |

[Exec] 52

26

F I G. 4

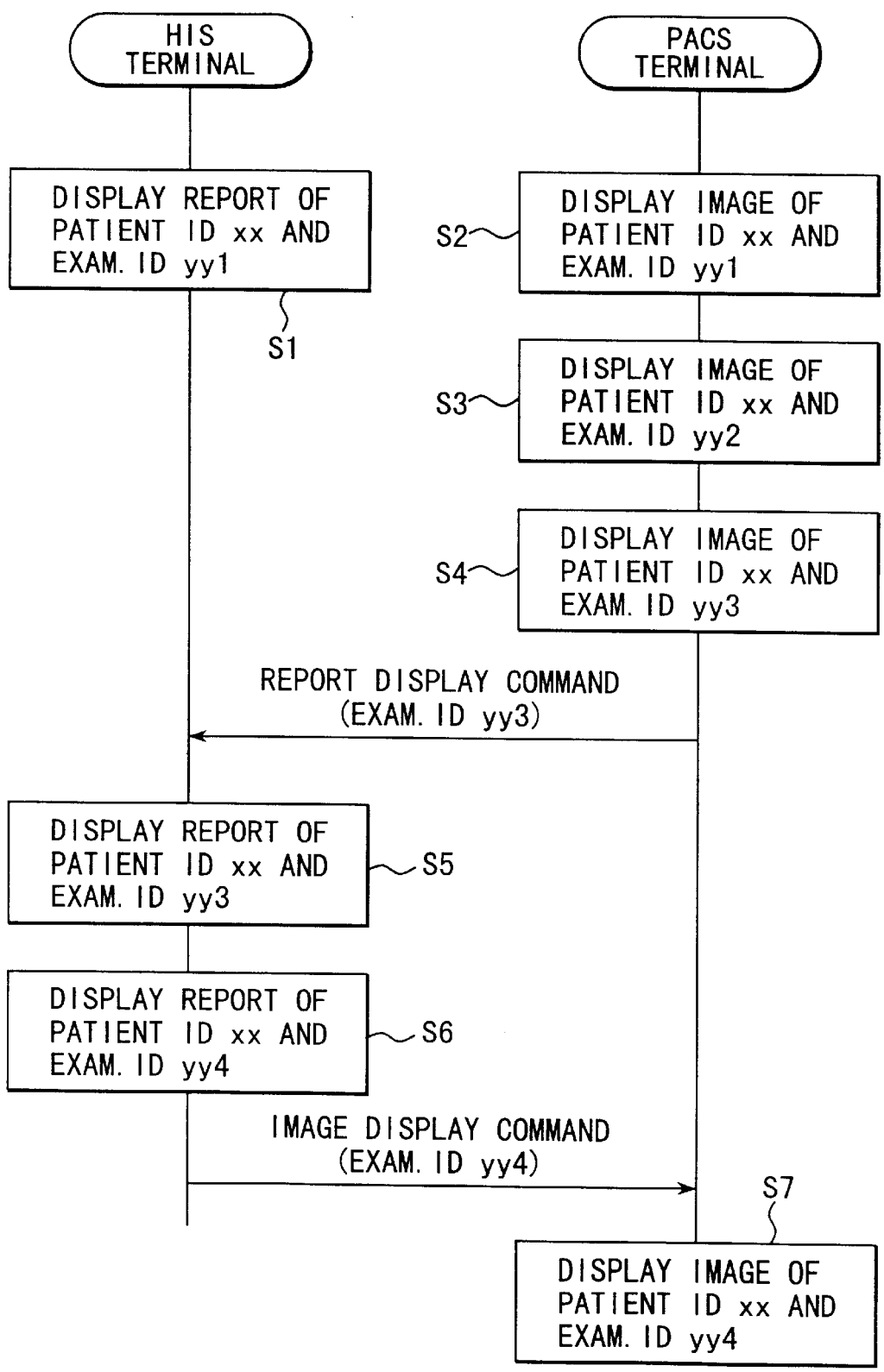
F I G. 7

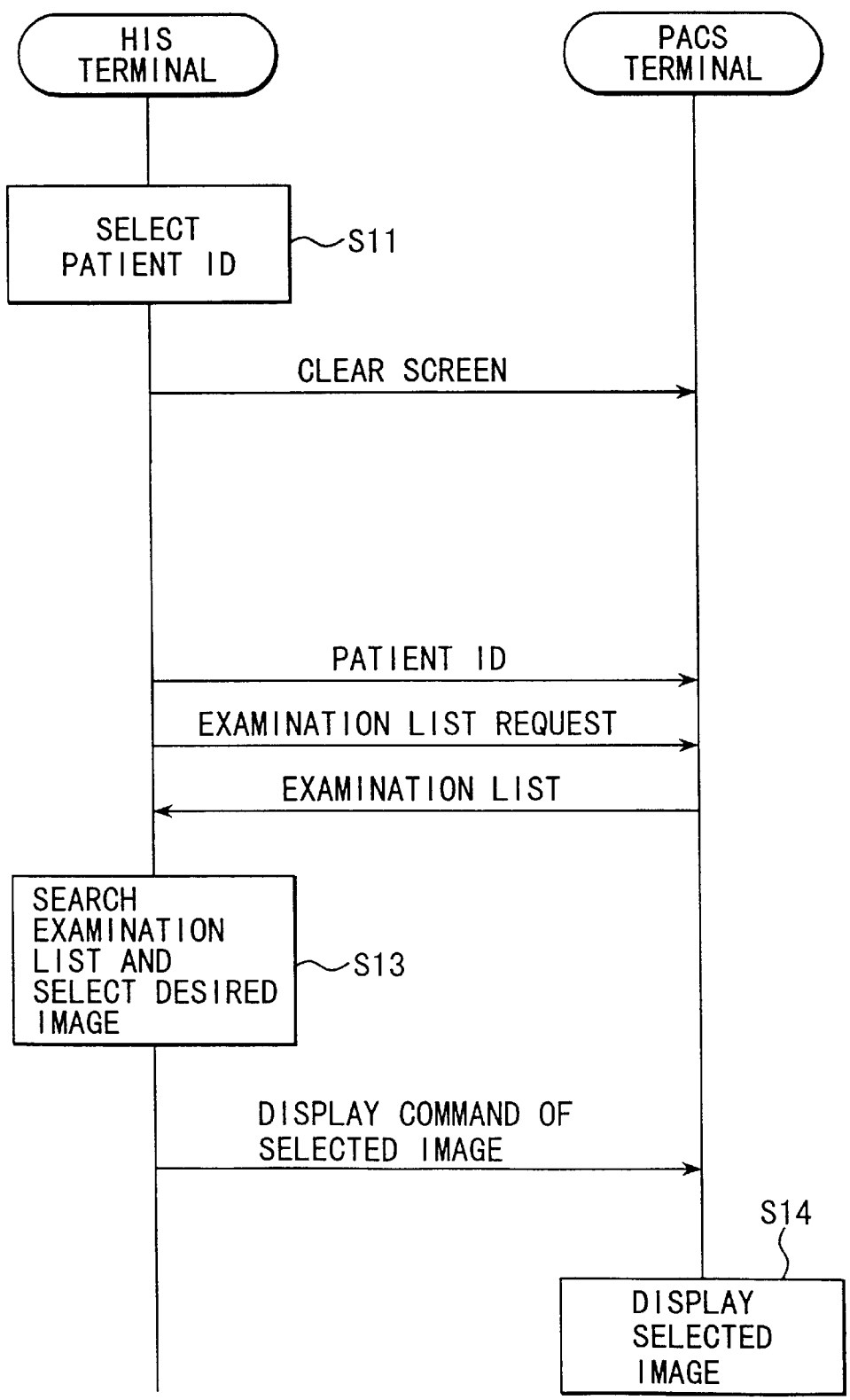
F I G. 8

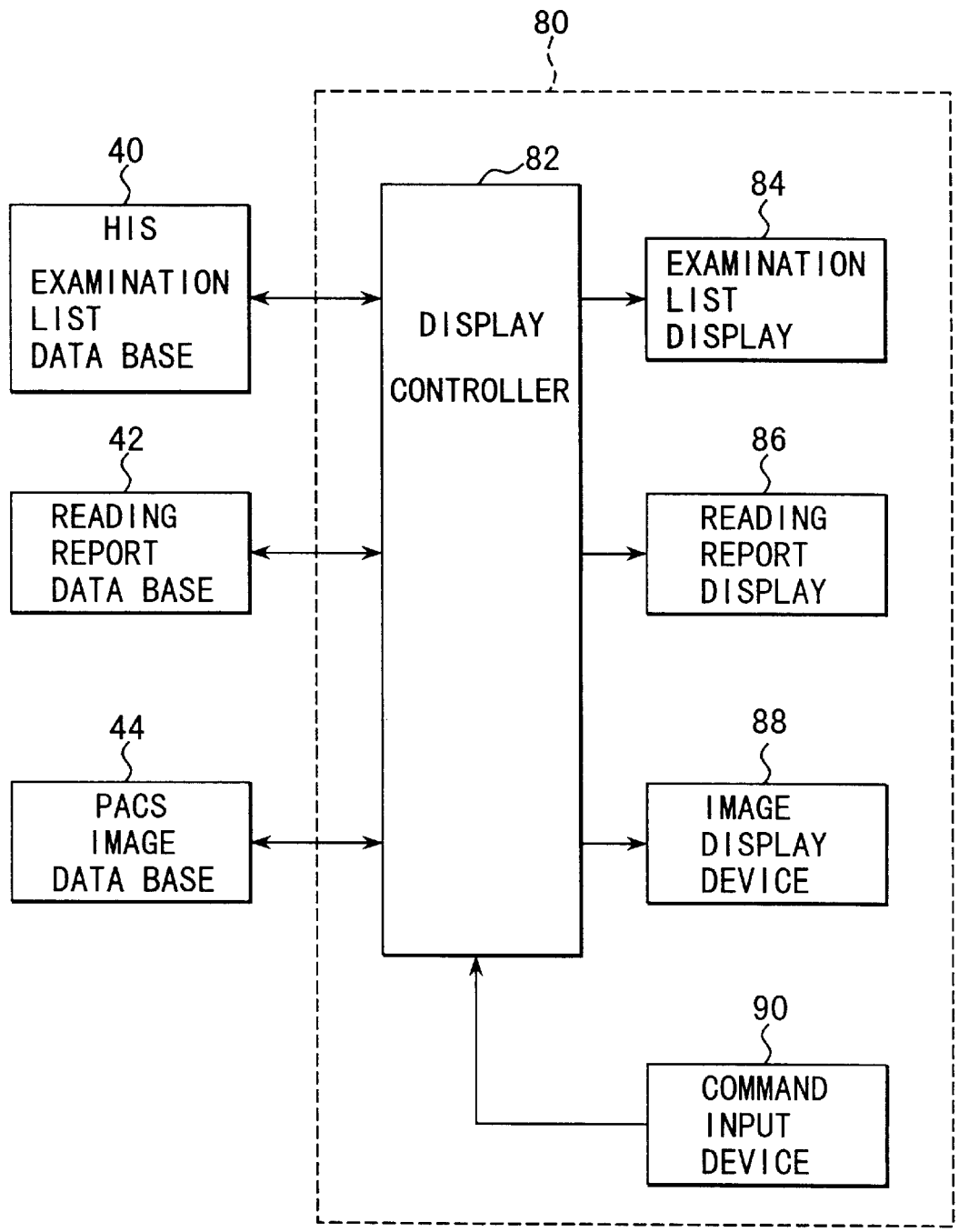
F I G. 9

INTEGRATED MEDICAL INFORMATION SYSTEM FORMED OF TEXT-BASED AND IMAGE-BASED DATABASES, AND DISPLAY THEREOF

BACKGROUND OF THE INVENTION

The present invention relates to a medical information system for managing and displaying medical information, such as charts and reading reports.

This application is based on Japanese Patent Application No. 08-144535, filed Jun. 6, 1996, the content of which is incorporated herein by reference.

When a medical care is performed in an outpatient clinic or a sick ward of a hospital, medical information, such as charts, medical images and reading reports are important reference information with which a doctor diagnoses. The doctor first makes a reference to the chart. The reading report is, as one of results of examinations, filed in the chart together with other results of examinations (such as a blood examination) to which a reference will be made. The medical image, such as an X-ray image, is filed in a film holder so as to be referred simultaneously with the related chart and the reading reports. The above-mentioned items of information have been stored and managed in the form of analog information, such as paper or a file.

In recent years, a medical information system for electronically managing medical information has been researched and developed. As one of the medical information systems, a hospital information system (hereinafter called as an "HIS") based on text data, such as charts and reading reports, has been developed. A conventional HIS includes an examination ordering system, an accounting system, a specimen examination system, a medicine system, chart managing system and the like. The HIS receives inputting of an order (an instruction to perform examinations) and results of the examinations and manages data of biochemical examinations, reading reports and the like mainly composed of text data or characters. The items of managed text data are displayed on a CRT or the like so as to be presented to the doctor.

Meantime, diagnosis of medical images has been performed such that an order is input from an HIS terminal device disposed in an outpatient clinic or a sick ward. However, the medical image is not displayed by the HIS terminal device. The reason for this is that the medical image has a considerably large size (for example, an X-ray image has a size of 2000 pixels×2000 pixels×12 bits) which cannot be sufficiently displayed by the HIS terminal device which is designed for displaying the text data due to its resolution and data transfer speed. Therefore, in medical facilities having the HIS, a reference has been made to an analog film stored in a film holder when a reference to an image must be made together with text data.

Therefore, there arises a requirement for displaying a medical image together with the text data on a CRT display device to enable an electronic reference. Thus, a variety of methods capable of realizing this electronic reference have been developed and researched. At present, the following methods have been established:

(1) An image is fetched (received) from another system for managing images, for example, a picture archive and communication system (PACS) in such a manner that the size of the image is reduced (compressed) to a size, for example, 512 pixels×512 pixels, which can be treated by the HIS terminal device so as to display the reduced image by the HIS terminal device together with the text data.

However, since the above-mentioned system is arranged to compress the image, the display image quality is too poor to realize a diagnosing accuracy acceptable for respiratory internal medicine, ortho-paedic surgery, cerebral surgery and urinology in which image diagnoses are performed frequently.

(2) It might therefore be considered feasible to employ a system in which a precise image display terminal device for another system for managing images, for example, the PACS, is provided for the HIS terminal device so as to display a precise image.

Although the above-mentioned system is able to realize a satisfactory image quality, the PACS terminal device and the HIS terminal device must independently be operated to display an image and the text data, thus the system cannot easily be operated. Therefore, a satisfactory large throughput for use in daily diagnoses cannot easily be realized.

As described above, the above-mentioned system is not a system which can be employed as a practically satisfactory system.

Although the convention medical information system is, as described above, able to convert character information, such as charts, reading reports and results of examinations, into electronic data (text data) which can easily be stored so as to be electronically displayed on a display screen, such as a CRT, in order to present information to a doctor, a precise medical image cannot be stored together with the text data so as to be displayed.

BRIEF SUMMARY OF THE INVENTION

In view of the foregoing, an object of the present invention is to provide a medical information system with which information, such as charts, medical images, reading reports and results of examinations, required to perform a diagnosis can be formed into electronic data to be stored and electronic data can be displayed on a screen to provide information for a doctor.

Another object of the present invention is to provide a medical information system which retrieves examination information and can automatically display a desired image and a corresponding reading report.

Still another object of the present invention is to provide an image terminal device of a picture archive and communication system which is connected to a character terminal device of a hospital information system for managing character information and operates interlocking with screen change of the character terminal device of the hospital information system.

Further object of the present invention is to provide a character terminal device of a hospital information system which is connected to an image terminal device of a picture archive and communication system for managing image information and operates interlocking with screen change of the image terminal device of the picture archive and communication system.

According to one aspect of the present invention, there is provided a medical information system comprising first display means for displaying medical information of a patient, the medical information comprising text data, second display means for displaying a medical image information corresponding to the medical information, and means for retrieving information which is to be displayed by one of the first display means and the second display means in accordance with identification information for identifying information which is displayed by the other of the first display means and the second display means.

According to another aspect of the present invention, there is provided a display terminal apparatus of a picture archive and communication system for storing a medical image and which is connected to a display terminal apparatus of a hospital information system for storing examination information which is formed of text data, the apparatus comprising an interface for receiving identification information from the display terminal apparatus of the hospital information system for identifying an examination, means for displaying an image relating to an examination which is identified by the identification information received by the interface, means for changing the image displayed by the display means to an image relating to another examination, and an interface for supplying a display command to the display terminal apparatus of the hospital information system for requesting display of an examination information relating to the other examination.

According to still another aspect of the present invention, there is provided a display terminal apparatus of a hospital information system for storing an examination information formed on text data and which is connected to a display terminal apparatus of picture archive and communication system for storing a medical image medical image, the apparatus comprising an interface for receiving identification information from the display terminal apparatus of the picture archive and communication system for identifying an examination, means for displaying examination information relating to an examination which is identified by the identification information received by the interface, means for changing the examination information displayed by the display means to examination information relating to another examination, and an interface for supplying a display command to the display terminal apparatus of the picture archive and communication system for requesting display of an image relating to the other examination.

According to the medical information system of the present invention, information, such as charts, medical images, reading reports and results of examinations, required to perform a diagnosis can be formed into electronic data to be stored and retrieved and electronic data can be displayed on a screen to provide information for a doctor.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a detailed block diagram showing the structure of a terminal devices of the first embodiment;

FIG. 3 shows a display example of a list of patients in the HIS terminal device;

FIG. 4 shows a display example of a list of examinations in the HIS terminal device;

FIG. 7 is a flow diagram showing an interlocking display of the HIS terminal device and the PACS terminal device;

FIG. 8 is a flow diagram showing an automatic display based on the data base retrieval; and FIG. 9 is a block diagram showing the structure of a second embodiment of the medical information system according to the present invention.

DETAILED DESCRIPTION OF THE INVENTION

A preferred embodiment of a medical information system according to the present invention will now be described with reference to the accompanying drawings.

Figure 1:
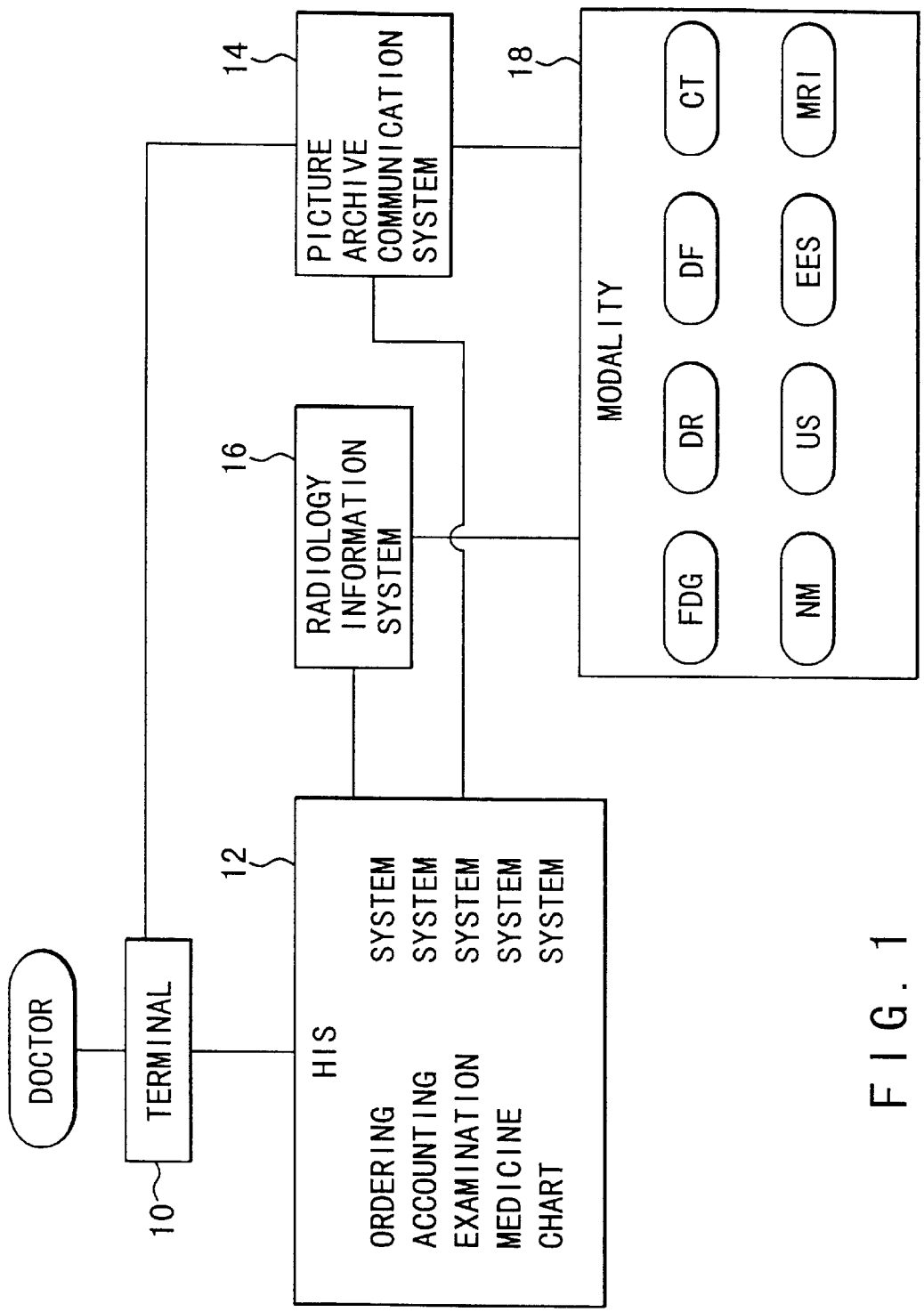
FIG. 1 is a block diagram of an whole medical information system of a first embodiment of the present invention.

FIG. 1 shows a block diagram of an entire system according to the first embodiment. THIS is an integration of an HIS and a PACS. An terminal device 10 which is accessed by a doctor is connected to an HIS 12 and a PACS. The HIS 12 includes an examination ordering system, an accounting system, a specimen examination system for storing a result of a specimen examination, a medicine system for managing a medicine given to a patient, chart managing system and the like. The HIS receives inputting of an order (an instruction to perform examinations) and results of the examinations and manages data of biochemical examinations, reading reports and the like mainly composed of text data or characters. The HIS 12 manages data in unit of examination. Therefore, each examination is identified by an examination ID. These data are displayed on a CRT or the like of the terminal device 10 so as to be presented to the doctor. The RIS (Radiography Information System) 16 and the PACS 14 are connected to a modality 18 which includes, for example, a film digitizer (FDG), a digital radiography (DR), a digital fluorography (DF), an X-ray computed tomography (CT), nuclear medicine diagnosis apparatus (NM), an ultra-sonic diagnosis apparatus (US), an electronic endoscope (EES), a magnetic resonance imaging apparatus (MRI). The PACS 14 collects images and stores the images with an additional information, such as a patient ID, name of patient, imaging condition, and imaging year/month/date. One examination may include plural images. A special reading doctor (usually, radiologist) reads images relating to one examination and writes a reading report for every examination.

FIG. 2 is a detailed block diagram showing a main part (the terminal device 10) of the first embodiment. The terminal device 10 is formed of an HIS terminal device 22 and a PACS terminal device 24. The HIS terminal device 22 comprises an examination list display device 26, a reading report display device 28, a display controller 30 for controlling the display devices 26 and 28, and a command input device 32 for inputting various commands for the controller 30. It is not necessary to provide physically separated two devices for the display devices 26 and 28. The examination list and the reading report may be displayed on the same display screen side by side or time-divisional manner. The display devices 26 and 28 display text data so that they are not required a high resolution. For example, it is sufficient for the display devices 26 and 28 to display 800 pixels×800 pixels×8 bits which is the same as a general personal computer. The PACS terminal device 24 comprises an image display 34, a display controller 36 for controlling the display device 34 and a command input device 38 for inputting various commands for the controller 36. The display devices 34 displays a medical image so that it is required a high resolution, at least 2000 pixels×2000 pixels×12 bits.

The HIS terminal device 22 is connected to an examination list data base 40 in the HIS 12 for storing a history of examinations (image diagnosis) for every patient and a reading report data base 42 in the PACS 14 for storing a reading report for every examination. The PACS terminal device 24 is connected to an image data base 44 in the PACS 14. The image data base 44 stores the image data with an additional information which is collected by the modality 18.

The display controller 30 of the HIS terminal device 22 and the display controller 36 of the PACS terminal device 24 are connected to each other. The HIS terminal device 22 and the PACS terminal device 24 can be operated in an interlock manner. As a result, both high quality image and detailed reading report can be displayed in a simplified operation. Specifically, when the reading report display device 28 of the HIS terminal device 22 displays a reading report of a given examination, a corresponding image collected by the given examination can be displayed by the image display device 34 of the PACS terminal device 24 in a high quality in response to a command from the HIS terminal device 22. Alternately, when the image display device 34 of the PACS terminal device 24 displays an image collected by a given examination, a reading report corresponding to the given examination can be displayed by the reading report display device 28 of the HIS terminal device 22 in response to a command from the PACS terminal device 24.

The operation of this embodiment having the above-mentioned structure will now be described.

EXAMPLE 1

When a doctor diagnoses a patient, he or she inputs a predetermined command from the command input device 32 of the HIS terminal device 22 so that a list of IDs of the patients registered in the HIS is displayed on the examination list display device 26. An example of the patient ID list display is shown in FIG. 3. The doctor selects the ID of the patient to be diagnosed and operates an execution button 50. The patient ID may be directly inputted without being selected in the list.

When the patient ID is selected or inputted, the HIS terminal device 22 reads the examination list of the selected patient from the examination list data base 40. The read examination list is displayed on the examination list display 26. An example of the examination list display is shown in FIG. 4. The doctor selects a desired examination and operates an execution button 52. It is assumed that the newest examination "Chest X-ray, 1995/12/1" is selected.

Figure 5:
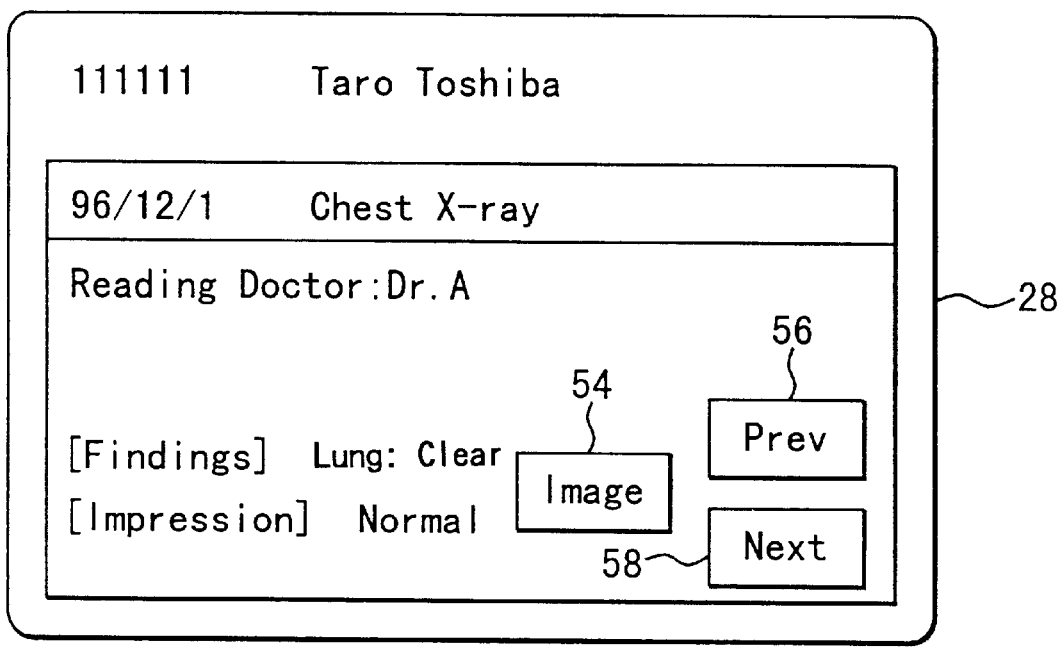
FIG. 5 shows a display example of a reading report in the HIS terminal device.

When the examination name (or ID) is selected, the HIS terminal device 22 reads the reading report of the selected examination from the reading report data base 42. The read reading report is displayed on the reading report display 28. An example of the reading report display is shown in FIG. 5. As described above, the display devices 26 and 28 may be realized by the same device and the examination list and the reading report may be displayed in a time-divisional manner. The reading report comprises a patient name, an examination date, an imaging portion, a name of the reading doctor, findings, an impression, and the like. The display screen also includes an image button 54, a previous button 56 and a next button 58. When the previous button 56 or the next button 58 is operated, the previous or next examination report of the same patient can be displayed. When the image button 54 is operated, in order to display an image corresponding to the displayed reading report, an image display request command including an examination ID corresponding to the displayed reading report is supplied to the display controller 36 of the PACS terminal device 24 from the display controller 30 of the HIS terminal device 22.

Figure 6:
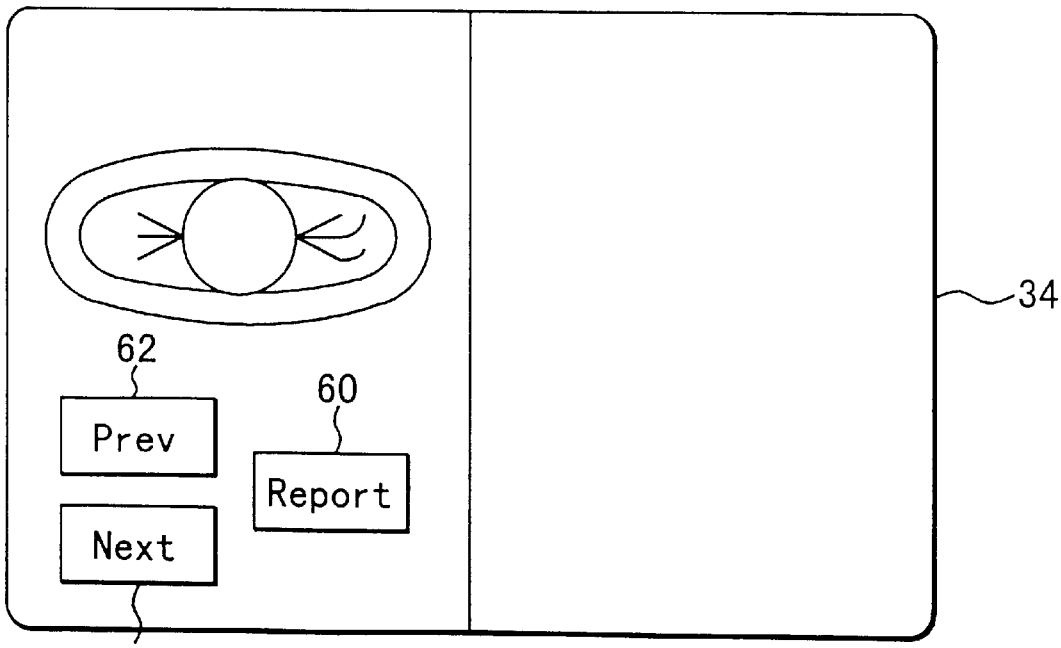
FIG. 6 shows a display example of an image in the PACS terminal device.

When the PACS terminal device 24 receives the image display request command, an image corresponding to the examination identified by the examination ID is displayed on the image display device 34. Plural images are collected in one examination, a predetermined image, for example, the first image is displayed. If another image collected by the examination is to be displayed, a given command is input from the command input device 38 in the same manner as in the usual PACS. FIG. 6 shows an example of image display. FIG. 6 is a partial display mode in which an image is displayed only in a half screen. The display mode is not limited to the partial mode, but may be a full screen mode.

Though not shown in FIG. 6, an additional information (text data) such as a patient name is displayed with the image. The display screen also includes a report button 60, a previous button 62 and a next button 64. When the previous button 62 or the next button 64 is operated, an image of the previous or next examination of the same patient can be displayed. When the report button 60 is operated, in order to display a reading report corresponding to the displayed image, a report display request command including an examination ID corresponding to the displayed image is supplied to the display controller 30 of the HIS terminal device 22 from the display controller 36 of the PACS terminal device 24. When the HIS terminal device 22 receives the report display request command, a reading report corresponding to the examination identified by the examination ID is displayed on the reading report display device 28.

As described above, the image/report display request command for a given examination ID is transferred between the HIS terminal device 22 and the PACS terminal device 24. Therefore, the reading report displayed by the HIS terminal device and the image displayed by the PACS terminal device are inter-lockingly changed. It is possible to simultaneously display both a reading report of a desired examination and a corresponding image in a simplified operation.

An example of an operation flow of the inter-locking change of the reading report and the image is shown in FIG. 7. The HIS terminal device 22 displays a reading report of an examination indicated by the examination ID "yy1" and of a patient indicated by the patient ID "xx" (step S1). At the same time, the PACS terminal device 24 displays the first image collected by the examination indicated by the examination ID "yy1" and of the patient indicated by the patient ID "xx" (step S2). If this image is not a desired one, a doctor operates the next button 64 on the image display device 34 of the PACS terminal device 24. The first image collected by an examination indicated by the examination ID "yy2" and of the patient indicated by the patient ID "xx" is displayed (step S3), the first image collected by an examination indicated by the examination ID "yy3" and of the patient indicated by the patient ID "xx" is displayed (step S4) and so on. When the desired image is displayed, the doctor operates the report button 60 on the image display device 34 of the PACS terminal device 24. Then, the report display command including the examination ID "yy3" is transferred to the HIS terminal device 22.

When the HIS terminal device 22 receives the report display command, the device 22 displays an examination report of an examination indicated by the examination ID "yy3" and of a patient indicated by the patient ID "xx" (step S5). If this report is not a desired one, a doctor operates the next button 58 on the reading report display device 28 of the HIS terminal device 22. An reading report of an examination indicated by the examination ID "yy4" and of a patient indicated by the patient ID "xx" is displayed (step S6) and so on. When the desired reading report is displayed, the doctor operates the image button 54 on the reading report display device 28 of the HIS terminal device 22. Then, the image display command including the examination ID "yy4" is transferred to the PACS terminal device 24.

When the PACS terminal device 24 receives the image display command, the device 22 displays an examination report of an examination indicated by the examination ID "yy4" and of a patient indicated by the patient ID "xx" (step S7). Hereinafter, when the examination ID is changed by one of the HIS terminal device and the PACS terminal device, the changed ID is transferred to the other so the display screen is changed interlockingly.

In the above operation, the image/report display command was manually input by using the image button 54 or report button 60. However, it is possible to automatically change both the display screens of the HIS and PACS terminal devices if the examination ID is changed by one of the HIS terminal device 22 and the PACS terminal device 24.

EXAMPLE 2

In the above example, an image to be displayed on the PACS terminal device is manually selected by a doctor. There will be described another example in which the HIS terminal device retrieves images satisfying a desired condition.

FIG. 8 shows this image retrieval display.

In the same manner as in the example 1, a list of IDs of the patients registered in the HIS is displayed on the examination list display device 26, as shown in FIG. 3, and the ID of the patient to be diagnosed is selected (step S11). Though the description is omitted in the example 1, a screen clear command is supplied from the HIS terminal device 22 to the PACS terminal device 24 in order to erase the displayed image. This is because an erroneous diagnosis is prevented.

In step S13, the HIS terminal device 22 retrieves the examination IDs includes in the examination list to select an examination ID/IDs which satisfy a predetermined condition. A display command of the selected image/images is transferred from the HIS terminal device 22 to the PACS terminal device 24. The selected image is displayed in step S14.

The following conditions are included in the predetermined condition for retrieving the examination to select an image to be displayed.

(1) An examination having an image which has been read by a reading doctor but has not been referred by a consultation doctor is retrieved.

Whether or not the image is not referred by the doctor can be determined by providing a viewed-flag in an examination data (FIG. 4) or determining by the HIS terminal device whether or not the reading report is present.

(2) An examination having an image which has been marked as an important image for the patient by the consultation doctor or an examination marked as an important examination image for the patient by the consultation doctor is retrieved.

(3) Images of all examinations or the newest examination for the patient are retrieved in response to an input of a patient identification information in a case where the input of the patient identification information is a first input after a consultation group for the patient has been changed. The consultation group includes a consultation department, a consultation room, a hospital ward. The change of the consultation group includes a case in which an outpatient is hospitalized at a different department at the time of outpatient and a case in which a hospitalized patient is discharged from a hospital. Further, the change of the consultation group includes a case in which the above mentioned change is occurred between a previous consultation day and a present consultation day for the patient.

The retrieving condition may be arbitrary modified.

Following examination includes images which have not been referred by the consultation doctor (the above condition (1)).

(a) An examination performed after a previous consultation day and a present consultation day and an examination to be performed at the present consultation day.

(b) An examination whose images are registered into the PACS data base on the present consultation day.

(c) An examination ordered at the previous consultation day.

(d) An examination (whose data comprising a flag indicating whether or not the image is displayed) does not have a flag indicating the image is displayed.

Example 2 automatically display any image/report that the doctor has not examine (or has not explained to the patient). The doctor then examines the image/report even if he or she has forgotten to examine it. Thus, Example 2 helps to enhance the efficiency of diagnosis.

EXAMPLE 3

Example 3 is a modification of Example 2 described above. In Example 3, the following sequence of steps is performed after the patient ID is selected and the screen clear command to the PACS is requested.

First, the HIS terminal device 22 supplies the patient ID and the examination list request command to the PACS terminal device 24. The PACS terminal device 24 has a buffer memory such as a hard disk drive to pre-fetch the images from an optical disk provided in the PACS. This is because the speed at which image data is read from the optical disk is low. Only the images stored in the buffer memory can be displayed by the display device 34. The examination IDs of the images stored in the PACS terminal device 24 are detected by the HIS terminal device 22 when the device 22 generates the examination list request command. Hence, the device 22 generates no image display command for an image not stored in the PACS terminal device 24. If the PACS display terminal device 24 receives an image display command from the HIS terminal device 22, the examination list of the images stored in the device 24 is supplied from the device to the HIS terminal device 22.

The number of examinations specified in the examination list associated with the patient ID could therefore be decreased in step S13.

In Example 3, any image data representing the image that should be displayed never happens to be absent in the PACS terminal device 24. It is therefore unnecessary to access the optical disk to fetch such image data therefrom. (In other words, no image represented by data fetched from the optical disk is displayed.) Hence, images can be displayed quickly in step S14.

As described above, according to this embodiment, the examination list for representing the history of examinations for the patient, the reading report for representing the impression of the reading doctor, and the image can be mutually referred from both of the HIS terminal apparatus and the PACS terminal apparatus. As a result, medical information, such as charts, medical images, reading reports, results of examinations, which are required to perform a diagnosis, can be converted into electronic data which can easily be stored and retrieved, thereby enabling the above information to be displayed on a display screen so as to provide information for a doctor. A medical care can be performed in accordance with information displayed on the display screen. Thus, a system can be established in place of the conventional system based on films and charts. As a result, quality of the service for patients and efficiency of the medical operations can be improved.

Another embodiment of the present invention will now be described.

Although the first embodiment has the structure in which the HIS terminal device 22 and the PACS terminal device 24 are physically independently provided, a second embodiment has a structure attempted such that the functions of the foregoing two terminal devices can be realized by a single terminal device.

As shown in FIG. 9, an examination data base 40, a reading report data base 42, and an image data base 44 are connected to a display controller 82 of a medical information terminal device 80. The terminal device 80 comprises an examination list display device 84, a reading report display device 86, an image display device 88, and a command input device 90. It is not necessary to provide physically separated three devices for the examination list display device 84, reading report display device 86, and image display device 88. The examination list, reading report, and image may be displayed on the same display screen side by side or time-divisional manner.

According to the second embodiment, it is possible by using the command input device 38 to retrieve and display the corresponding reading report and image belonging to the same examination for the same patient, independently retrieve and display the examination list, reading report and the image and perform display such that another information item is synchronized with any one of the examination list, reading report and the image which are being displayed.

The present invention is not limited to the above-mentioned embodiments and a variety of modifications are permitted. For example, although in the first embodiment the HIS terminal device 22 and the PACS terminal device 24 are directly connected to each other by generally using a direct digital connection method, such as RS-232C or SCSI, they may be connected through a network, such as Ethernet, FDDI or ATM.

As described above, according to the present invention, a medical information system can be provided which is able to convert information, such as charts, medical images, reading reports, results of examinations, which are required to perform a diagnosis, into electronic data which can easily be stored and retrieved and which enables the above information to be displayed on a screen so as to provide information for a doctor.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical information system comprising:
   a first database configured to store medical documents formed of text and corresponding to respective identification data;
   a first command input device configured to input a first rage display command and a first document display command, both of the first commands including the identification data;
   a first database controller configured to retrieve and display a medical document from said first database based on the first document display command;
   a second database configured to store medical images corresponding to the medical documents;
   a second command input device configured to input a second image display command and a second document display command, both including the identification data;
   a second database controller configured to retrieve and display a medical image from said second database based on the second image display command;
   wherein said first database controller is configured to transmit the first image display command to said second database controller so that said second data controller retrieves and displays a medical image from said second database based on the first image display command and said second database controller is configured to transmit the second document display command to said first database controller so that said first database controller retrieves and displays a medical document from said first database on the second document display command, whereby a medical document and a medical image corresponding to the displayed medical document are interlockingly displayed.

2. A medical information system according to claim 1, wherein said first database controller comprises a first display configured to display the retrieved medical document and said second database controller comprises a second display configured to display the retrieved medical image and said first and second displays are provided close to each other.

3. A medical information system according to claim 1, in which said identification data is examination identification data.

4. A medical information system according to claim 1, wherein said first or second database controller transmits the first image display command or the second document display command to said second or first database controller when the identification data is changed.

5. A medical information system according to claim 1, wherein patient identification data is input by one of said first and second command input devices after a patient has been hospitalized.

6. A medical information system according to claim 1, wherein patient identification data is input by one of said first and second command input devices after a patient has been discharged from a hospital.

7. A medical information system according to claim 1, wherein patient identification data is input by one of said first and second command input devices after a consultation department for a patient has been changed.

8. A medical information system according to claim 1, wherein patient identification data is input by one of said first and second command input devices after a consultation room for a patient has been changed.

9. A medical information system according to claim 1, wherein patient identification data is input by one of said first and second command input devices after a hospital ward for the patient has been change.

10. A medical information system according to claim 1, wherein when patient identification data is included in a command transmitted to one of said first and second database controller, the other of said first and second database controllers retrieves such data from one of said first and second databases that satisfies a predetermined condition.

11. A medical information system according to claim 10, in which said predetermined condition is that data is marked as important data.

12. A medical information system according to claim 10, in which said predetermined condition is that the data relates to an examination marked as an important examination.

13. A medical information system according to claim 10, in which said predetermined condition is an unviewed image which is not referred by a doctor.

14. A medical information system according to claim 13, in which the unviewed image is an image collected in an examination performed between a previous consultation day and a present consultation day for a patient.

15. A medical information system according to claim 13, in which existence of the unviewed image for a patient is detected based on existence of an examination scheduled on a present consultation day.

16. A medical information system according to claim 13, in which existence of the unviewed image for a patient is detected based on existence of an examination registered to said medical information system on a present consultation day.

17. A medical information system according to claim 13, in which existence of the unviewed image for a patient is detected based on existence of an examination ordered on a previous consultation day.

18. A medical information system according to claim 13, in which the unviewed image is an image which is not provided with a flag indicating a fact that the image has been displayed.

19. A medical information system according to claim 13, in which the unviewed image is an image provided with a flag indicating a fact that the image has not been displayed.

20. A medical information system according to claim 10, in which the medical image which satisfies the predetermined condition is an image which has been read by a reading doctor but has not been referred by a consultation doctor.

21. A medical information system according to claim 20, in which whether or not the image has been read is determined based on whether or not a flag indicating that the image has been read exists.

22. A medical information system according to claim 20, in which whether or not the image has been read is determined based on whether or not a flag indicating that the image has not been read does not exist.

23. A medical information system according to claim 20, in which whether or not the image has been read is determined based on existence of a reading report of the image.

24. A medical information system according to claim 1, in which said identification data represents a type of examination and a date of examination.

25. A display apparatus of a picture archiving and communication system (PACS) which stores medical images and is configured to be connected to a hospital information system (HIS) which stores examination documents comprising text data and includes au (HIS) display apparatus for displaying an examination document, comprising:

a PACS display;

an interface configured to receive a image display command from said HIS, the image display command including identification data identifying an examination corresponding to the examination document displayed on the HIS display apparatus; and a display controller configured to retrieve an image relating to the examination identified by the identification data received by said interface and to supply a retrieved image to the PACS display so that the medical image displayed by the PACS display is changed interlockingly with changes in the examination document displayed by the HIS play apparatus.

26. A display apparatus according to claim 25, further comprising an input device for changing the image displayed to another image relating to another examination by inputting identification data identifying the other examination.

27. A display apparatus of a hospital information system (HIS) which stores examination documents comprising text data and is configured to be connected to a picture archiving and communication system (PACS) which stores medical images and includes a PACS display apparatus for displaying a medical image, comprising:

an HIS display;

an interface configured to receive a document display command from said PACS, the document display command including identification data identifying an examination corresponding to the medical image displayed on the PACS display apparatus; and a display controller configured to retrieve an examination document relating to the examination which is identified by the identification data received by said interface from said PACS and to supply a retrieved examination document to the HIS display so that the examination document displayed by the HIS display is changed interlockingly with changes in the medical image displayed on the PACS display apparatus.

28. A display terminal apparatus according to claim 26, further comprising:

a display for displaying a list of examination information in response to input of patient identification data;

a selector for selecting an examination from the list of examination information; and a display for displaying a detail of the examination information of the selected examination.

29. A display terminal apparatus according to claim 26, further comprising:

a controller for retrieving predetermined examination information for a patient in response to input of identification data of a patient; and a display for displaying the predetermined examination information retrieved by said controller.

30. A display terminal apparatus according to claim 28, in which said controller retrieves examination information corresponding to a medical image which has been read by a reading doctor but has not been referred to by a consultation doctor.

31. A display terminal apparatus according to claim 28, in which said controller retrieves examination information marked as important examinations or examination information corresponding to an image marked as an important image.

32. A display terminal apparatus according to claim 28, in which said controller retrieves all examination information of the patient in a case where the input of the patient identification data is a first input after a consultation group in a hospital for the patient has been changed.

33. A medical information system according to claim 1, wherein said second database comprises a low-speed large capacity storage device configured to store all of the medical images and a high-speed small capacity storage device configured to store some of the medical images.

* * * * *